United States Patent [19]

Tanaka et al.

[11] Patent Number: 5,185,461
[45] Date of Patent: Feb. 9, 1993

[54] PROCESS FOR PREPARING 2-AMINOETHYL ESTERS OF METHACRYLIC ACID

[75] Inventors: Yasumasa Tanaka, Suita; Hideyuki Nishibayashi, Nishinomiya; Kouichi Tsuchitani, Suita; Hideyuki Tahara, Osaka, all of Japan

[73] Assignee: Nippon Shokubai Co., Ltd., Osaka, Japan

[21] Appl. No.: 761,383

[22] Filed: Sep. 18, 1991

[30] Foreign Application Priority Data

Sep. 20, 1990 [JP] Japan .................. 2-253138
Sep. 11, 1991 [JP] Japan .................. 3-231931

[51] Int. Cl.$^5$ .............................. C07C 69/52
[52] U.S. Cl. .................................... 560/222
[58] Field of Search ......................... 560/222

[56] References Cited

U.S. PATENT DOCUMENTS 3,336,358  8/1967  McFadden ............... 260/465.4
4,500,728  2/1985  Fazio et al. ............. 560/222

*Primary Examiner*—Paul J. Killos
*Attorney, Agent, or Firm*—Birch, Stewart, Kolasch & Birch

[57] ABSTRACT

A process for preparing 2-aminoethyl esters of methacrylic acid by the reaction of methacrylic acid with an aziridine compound in a reaction solvent consisting of water or an aqueous solvent.

9 Claims, No Drawings

PROCESS FOR PREPARING 2-AMINOETHYL ESTERS OF METHACRYLIC ACID

BACKGROUND OF THE INVENTION

1. Field of the Invention

The present invention relates to a process for preparing 2-aminoethyl esters of methacrylic acid (hereinafter referred to as 2-AEMA) by the reaction of methacrylic acid with an aziridine compound.

2. Discussion of Related Art

The 2-AEMA compounds produced by the present invention are useful compounds as raw material for dispersants, flocculants, coagulants, paper additives used for a retention aid, drainage aid, strength aid, thickening agent, adhesive, chelate resin, ion-exchange resin, resin for enhanced oil recovery, photo-resist material, enzyme carrier, antibacterial resin, and modifier and processing aid used for the manufacture of fibers, plastics, paints, inks, papers and other products.

For the preparation of 2-AEMA, for example, a process disclosed in U.S. Pat. No. 3336358 is conventionally known. According to this process, first, methacrylic acid (hereinafter referred to as MA) is brought to react with an aziridine compound (hereinafter referred to as Az) in a saturated (or an unsaturated) aliphatic hydrocarbon solvent. Next, an inorganic acid is added to the prepared 2-AEMA, and an inorganic salt of 2-AEMA is separated.

A process disclosed in U.S. Pat. No. 4500728 is known as a method which achieves improved yields of the desired product compared to the above process. In this process, 2-isopropenyl-2-oxazoline (hereinafter referred to as IPO) is added to an aqueous solution containing a specified acid, so that 2-AEMA of high purity is produced.

However, the process of U.S. Pat. No. 3336358 yields a low selectivity of the desired product, i.e. 2-AEMA, while forming large amounts of by-products. In addition, as 2-AEMA has a double bond, some parts of the 2-AEMA are converted to a polymer when the inorganic acid is added.

Meanwhile, the process of U.S. Pat. No. 4500728 requires a number of procedures for preparing the IPO, i.e. the raw material. Therefore, considering the yield of the 2-AEMA from the starting materials used for the preparation of IPO, the yield is extremely low due to the large number of procedures, thereby resulting in high manufacturing costs.

SUMMARY OF THE INVENTION

An object of the present invention is to provide a process for preparing 2-aminoethyl esters of methacrylic acid in high purity.

Another object of the present invention is to provide a process for preparing 2-aminoethyl esters of methacrylic acid which reduces its manufacturing costs.

In order to achieve the above objects, the reaction conditions were examined with respect to MA and Az for the preparation of 2-AEMA, and a process was discovered which achieves high yields of 2-AEMA with low manufacturing costs.

More specifically, the process for preparing 2-AEMA of the present invention is characterized in that a reaction solvent used for the reaction of MA and Az is water or an aqueous solvent.

In the present invention, 2-AEMA include, in addition to 2-aminoethyl ester which is formed by the reaction of 1 molecule of MA and 1 molecule of Az, esters which are formed by the additional reaction of Az to the amino group of 2-aminoethyl esters, i.e. by reaction of 1 molecule of MA and a plurality of molecules of Az. These esters are also useful compounds for the manufacture of the above-mentioned industrial products.

With the process of the present invention, water or an aqueous solvent having a high dielectric constant is employed as the reaction solvent. Accordingly, reaction will be promoted under conditions in which ionization takes place smoothly, thereby improving the yield of 2-AEMA with respect to the placed amount of aziridine compound. Moreover, since the produced 2-AEMA are stabilized as salt of methacrylic acid or inorganic acid, the yield will be improved.

Water or an aqueous solvent employed as the reaction solvent by the process of the present invention is less expensive than saturated or unsaturated aliphatic hydrocarbon solvents, for example, n-hexane used as the reaction solvent with a conventional process. In consequence, the manufacturing costs can be reduced. This process also allows the preparation of 2-AEMA at improved yields compared to the conventional process. In addition, there is an advantage that 2-AEMA of high purity can be obtained from the reaction solution through a very easy procedure.

DETAILED DESCRIPTION OF THE INVENTION

The following will describe in detail a process for preparing 2-aminoethyl esters of methacrylic acid relating to the present invention.

The selectivity termed herein is the ratio of Az (aziridine compound) used for the production of a desired product to Az introduced and is given by $P_A/F_A \times 100$, wherein $F_A$ represents the number of moles of introduced Az and $P_A$ the number of moles of Az in the prepared 2-AEMA.

As for Az, although not particularly restricted, ethyleneimine, propyleneimine, hydroxyethyl ethyleneimine, cyanoethyl ethyleneimine and aminoethyl ethyleneimine are preferable.

Regarding the reaction solvent, water is preferable, but an aqueous solvent can be used. The aqueous solvent is a mixture of water and a solvent which can be dissolved in water at any proportion. For instance, methanol, ethanol, isopropyl alcohol, acetonitrile, acetone, dimethyl sulfoxide, dimethylformamide, dioxane and tetrahydrofuran are used.

The proportion of water to the total reaction mixture is preferably in the range from 5 weight percent to 90 weight percent. The proportion of water means the proportion of the weight of water to the total weight of the introduced raw materials, i.e. MA, Az and solvent, i.e. water or aqueous solvent.

When water amounts to less than 5 weight percent, MA or a solvent which can be dissolved in water at any proportion is the major percent of the solvent in the reaction mixture. This suppresses ionization, and therefore the formation of a stable salt from 2-AEMA and MA is restrained. As a result, the selectivity of 2-AEMA is lowered. Meanwhile, when the proportion of water exceeds 90 weight percent, the dilution of the raw material increases and therefore the reaction rate is lowered, resulting in a lowering of the productivity. Thus, using water in excess or in reduced amounts of the above mentioned ranges causes unfavorable results.

When the number of moles of introduced MA in the reaction mixture is denoted as $F_M$ and the number of moles of the introduced Az as $F_A$, the mole ratio of $F_M$ to $F_A$ is in the range from ½ to 20/1, and more preferably 2/1 to 10/1. When the mole ratio of $F_M$ to $F_A$ introduced is smaller than ½, free MA as raw material in the reaction mixture decreases significantly as the amino group of the prepared 2-AEMA and MA form salt. This causes 2-AEMA to be produced in reduced amounts and a lowering of the selectivity. Further, when the ratio of $F_M$ to $F_A$ is greater than 20/1, large amounts of MA will have unreacted at the time the reaction is completed. Therefore, much time will be required to remove MA in refining, causing a lowering of the productivity.

As for a concrete method of reacting MA with Az, although not particularly restricted, it is desirable to control the mole ratio of acid to amine in the reaction mixture not to be below 1.5. This is because free MA needs to be present throughout the process in order to promote the reaction. However, when a basic substance, for example, amine is present in the reaction mixture, MA and the basic substance are ionic-bonded, producing a salt of MA. This salt does not contribute to the reaction for the formation of the desired product, thereby slowing the reaction rate.

To carry out the reaction promptly, the following two methods are listed.

In the first method, greater amounts of MA to amine is provided, so that free MA is present in the reaction mixture even when MA reacts with all the amine in the reaction mixture and forms salt. Namely, with this method, the reaction proceeds by maintaining the mole ratio of MA to amine in the reaction mixture at least 1.5.

In the second method, an inorganic acid, for example, nitric acid is added to the reaction mixture to substitute it for MA in the salt produced from MA and amine, whereby nitrate is formed. This permits free MA to be produced and the reaction to proceed. Namely, with this method the reaction is carried out by maintaining the ratio of an equivalent A of free MA to an equivalent B as base of Az, A/B, at least 1.5 (this method is especially effective when the mole ratio of introduced MA to amine does not exceed 1.5).

For example, a preferable reaction is carried by introducing Az dropwise into an aqueous solvent containing MA in the presence of a polymerization inhibitor, for example hydroquinone, or by introducing MA together with Az into an aqueous solvent.

The concentration of MA and Az in the reaction mixture is preferably within the range from 10 to 95 weight percent. A low concentration of no greater than 10 weight percent results in a decrease in the productivity. Meanwhile, with a high concentration in excess of 95 weight percent, Az which promotes the reaction is substantially dissolved in MA. This suppresses ionization, and therefore the formation of a stable salt from 2-AEMA and MA is restrained. In consequence, the selectivity is lowered.

The temperature is preferably in the range from 10° C. to 100° C., more preferably 20° C. to 80° C. A temperature lower than 10° C. results lessens the reaction rate, and thereby lowers productivity. Also, a temperature in excess of 100° C. promotes the formation of by-products. For instance, as shown in Formula (1) below, 2-AEMA is isomerized to an amide, which causes a lowering of the selectivity.

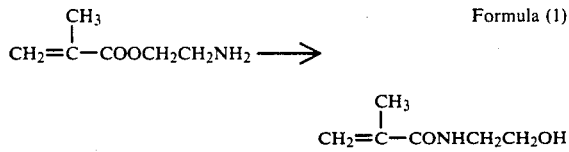

Pressure with respect to the reaction system is not particularly regulated. However, when an aqueous solvent contains a solvent whose boiling point is low, a reaction may be carried out under pressure.

When unreacted MA is removed, an inorganic acid salt solution of the prepared 2-AEMA may also be used. To obtain the inorganic acid salt solution of 2-AEMA, after the reaction of MA with Az in an aqueous solvent, an inorganic acid, for example, hydrochloric acid is added, and then unreacted MA is extracted and separated by means of a solvent which is insoluble in water, such as benzene, toluene and chloroform.

PREFERRED EMBODIMENTS

The following examples and comparative examples are presented for the purpose of illustration only, and are not to be construed as limiting the scope of the invention in any way.

EXAMPLE 1

344 grams of MA, 387 grams of deionized water and 3.44 grams of hydroquinone as polymerization inhibitor were placed into a reaction vessel, mixed and heated to 50° C. Then, while keeping the mixture at 50° C., 43 grams of ethyleneimine (hereinafter referred to as EI) as Az was added to the mixture dropwise in about 1 hour to carry out a reaction. Next, the temperature of the reaction mixture was maintained at 50° C. for 4 hours for aging to obtain 2-AEMA. The reaction solution was analyzed by liquid chromatography. The selectivity of EI added as Az was 94.8 percent. The reaction conditions and results are presented in Table 1.

Further, 103 grams of 35 percent hydrochloric acid aqueous solution was added to the reaction solution, and unreacted MA was removed by liquid-liquid extraction with toluene. Then the resulting solution was concentrated to yield 253 grams of aqueous solution containing 60 weight percent of 2-AEMA hydrochloride.

EXAMPLE 2

The same preparation procedures and analysis as in Example 1 were conducted except that aminoethyl ethyleneimine was employed instead of EI used in Example 1. The reaction conditions and results are presented in Table 1. According to the results, a selectivity as high as the one in Example 1 was obtained.

EXAMPLE 3

The same preparation procedures and analysis as in Example 1 were conducted except that a mixed solution of water and isopropyl alcohol (50/50 by weight) was used as reaction solvent instead of water in Example 1. The reaction conditions and results are presented in Table 1. This example also achieved a high selectivity similar to the one in Example 1.

EXAMPLE 4

The same preparation procedures and analysis as in Example 1 were conducted except that the mole ratio of MA to EI was varied to (1.6/1) from the mole ratio (4/1) in Example The reaction conditions and results are presented in Table 1.

As demonstrated by the results, this example achieved a high selectivity like Example 1.

EXAMPLE 5

The same preparation procedures and analysis as in Example 1 were conducted except that the mole ratio of MA to EI was varied to (1/1) from the mole ratio (4/1) in Example 1. The reaction conditions and results are presented in Table 1.

According to the results, an improved selectivity although lower than the one in Example 1 was achieved. In this example, salt was formed from unreacted MA and the amino group of the prepared 2-AEMA and stabilized, and which caused absence of free MA. The absence of free MA seemed to contribute to a decrease in the selectivity.

EXAMPLE 6

The same preparation procedures and analysis as in Example 1 were conducted except that the mole ratio of MA to EI was varied to (2/1) from the mole ratio (4/1) in Example 1. The reaction conditions and results are presented in Table 1.

This example also achieved a high selectivity like Example 1.

EXAMPLE 7

The same preparation procedures and analysis as in Example 1 were conduced except that the mole ratio of MA to EI was varied to (8/1) from the mole ratio (4/1) in Example 1 and the proportion of introduced MA and Az to the total weight of the reaction mixture was set at 89 weight percent by adjusting the amount of water as reaction solvent. The reaction conditions and results are presented in Table 1.

According to the results, even the total weight of MA and Az introduced was 89 weight percent, i.e. the proportion of water to the reaction mixture was 11 weight percent, a high selectivity was achieved like Example 1.

EXAMPLE 8

The reaction temperature was set at 30° C. In this case, as the reaction rate would decrease, the reaction mixture was maintained at 30° C. for 24 hours for aging. Further, the amount of water as reaction solvent was adjusted such that the proportion of MA and Az introduced amounted to 50 weight percent of the total weight of the reaction mixture. Except for these differences in conditions, the preparation procedures and analysis were conducted in the same manner as in Example 7. The reaction conditions and results are presented in Table 1.

According to the results, the time taken for reaction was longer compared to the one in Example 1. However, a high selectivity similar to the one in Example 1 was obtained with a reaction temperature of 30° C. which was almost equal to room temperature, i.e. without particularly heating the mixture.

EXAMPLE 9

The same preparation procedures and analysis as in Example 8 were conducted except that the reaction temperature was set at 60° C. The reaction conditions and results are presented in Table 1. According to the results, a high selectivity similar to the one in Example 8 was achieved.

EXAMPLE 10

Hydroxyethyl ethyleneimine was used as Az, and the mole ratio of MA to hydroxyethyl ethyleneimine was set at 2.5/1. Further, water used as reaction solvent was 30 weight percent. Except for these differences in conditions, the preparation procedures and analysis were conducted in the same manner as in Example 1. The reaction conditions and results are presented in Table 1.

As demonstrated by the results, a high selectivity similar to the one in Example 1 was obtained.

EXAMPLE 11

The same preparation procedures and analysis as in Example 1 were conducted except that a mixture of aminoethyl ethyleneimine and EI (9/1 by weight) was used as Az. The reaction conditions and results are presented in Table 1. As demonstrated by the results, a high selectivity similar to the one in Example 1 was achieved.

EXAMPLE 12

A process for preparing 2-AEMA at high selectivity was examined. With this process, the mole ratio of MA to Az was set at 2/1, and after a reaction an inorganic acid whose number of moles was the same as 2-AEMA formed in theory was added and then Az was added, so that it reacted with unreacted MA.

More specifically, 86 grams (about 1 mole) of MA, 108 grams of deionized water and 86 milligrams of methoquinone as polymerization inhibitor were placed into a reaction vessel and mixed, and then heated to 50° C. 21.5 grams (0.5 moles) of EI was introduced into the reaction mixture dropwise in about one hour while keeping the temperature of the mixture at 50° C., so that a reaction was carried out. Then, the reaction mixture was maintained at a temperature of 50° C. for 4 hours for aging. Further, 52.5 grams (about 0.5 moles) of 60 percent nitric acid was added and then 10.8 grams (about 0.25 moles) of EI was introduced dropwise in about 40 minutes to carry out a reaction. The reaction mixture was maintained at a temperature of 50° C. for 4 hours for aging to obtain 2-AEMA.

The reaction solution was analyzed by liquid chromatography, and the selectivity was 92.7 percent. It was found out through the examination of the obtained chromatogram that the proportion of 2-AEMA having a plurality of moles of Az with respect to one mole of MA increased. The reaction conditions and results are presented in Table 1.

According to the results, although the final mole ratio of MA to Az, 4/3, was almost equal to the mole ratio in Example 5, this example achieved a selectivity higher than the one in Example 5. This may be due to the fact that when nitric acid was added, it substituted for MA in salt produced from the prepared 2-AEMA and unreacted MA. Therefore, free MA increased and the reaction progressed.

EXAMPLE 13

The same process as in Example 12 was examine by further adding an inorganic acid and Az so that the 2-AEMA were produced at a high selectivity even when the ratio of MA to Az was smaller than 1/1.

More specifically, 86 grams (about 1 mole) of MA, 113 grams of deionized water and 86 milligrams of methoquinone as polymerization inhibitor were placed into a reaction vessel and mixed, and then heated at 50° C. 26.9 grams (0.625 moles) of EI was introduced into the reaction mixture dropwise in about one hour while maintaining the temperature at 50° C., so that a reaction was carried out. Then, the reaction mixture was maintained at a temperature of 50° C. for 4 hours for aging. 0.56 moles of unreacted MA resulted. Further, 65.6 grams (about 0.625 moles) of 60 percent nitric acid was added and then 15.0 grams (about 0.35 moles) of EI was introduced dropwise in about 40 minutes. The reaction mixture was maintained at a temperature of 50° C. for 4 hours for aging. The procedure for adding nitric acid and introducing EI was repeated four times. The total amount of EI introduced was 70.39 grams (1.64 moles) and the mole ratio of MA to EI was 1/1.64.

The reaction solution was analyzed by liquid chromatography, and the selectivity was 60.5 percent. Concerning this process, it was also found through the examination of the obtained chromatogram that the proportion of 2-AEMA having a plurality of moles of Az with respect to one mole of MA increased. The reaction conditions and results are presented in Table 1. As demonstrated by the results, an improved selectivity was achieved.

COMPARATIVE EXAMPLE 2

The same preparation procedures and analysis as in Comparative Example 1 were conducted except that n-hexane was used a reaction solvent instead of isopropyl alcohol and the reaction temperature was set at 60° C. The reaction conditions and results are presented in Table 2.

The results of Examples 1 to 13 and Comparative Examples 1 and 2 show that reaction mixture needs to contain water.

TABLE 2

| Comparative Example No. | Aziridine Compound | MA/Az (mole ratio) | Reaction Solvent | Concentration (wt %) | Temperature (°C.) | Selectivity to Aminoethyl Esters (%) |
| --- | --- | --- | --- | --- | --- | --- |
| 1 | ethyleneimine | 2/1 | isopropyl alcohol | 50 | 50 | 30.4 |
| 2 | ethyleneimine | 2/1 | n-hexane | 50 | 60 | 35.0 |

Az: aziridine compound, and MA: methacrylic acid.

The invention being thus described, it will be obvious that the same may be varied in many ways. Such variations ar not to be regarded as a departure from the spirit and scope of the invention, and all such modifications as would be obvious to one skilled in the art are intended to be included within the scope of the following claims.

What is claimed is:

1. A process for preparing 2-aminoethyl esters of methacrylic acid comprising reacting methacrylic acid and an aziridine compound in a reaction solvent medium selected from the group consisting of water and an aqueous solvent at a temperature in the range of from 10° to 100° C.

2. The process as defined in claim 1, wherein a pro-

TABLE 1

| Example No. | Aziridine Compound | MA/Az (mole ratio) | Reaction Solvent | Concentration (wt %) | Temperature (°C.) | Selectivity to Aminoethyl Esters (%) |
| --- | --- | --- | --- | --- | --- | --- |
| 1 | ethyleneimine | 4/1 | water | 50 | 50 | 94.8 |
| 2 | aminoethyl ethyleneimine | 4/1 | water | 50 | 50 | 98.7 |
| 3 | ethyleneimine | 4/1 | water.IPA | 50 | 50 | 90.3 |
| 4 | ethyleneimine | 1.6/1 | water | 50 | 50 | 85.6 |
| 5 | ethyleneimine | 1/1 | water | 50 | 50 | 73.3 |
| 6 | ethyleneimine | 2/1 | water | 50 | 50 | 92.4 |
| 7 | ethyleneimine | 8/1 | water | 89 | 50 | 93.0 |
| 8 | ethyleneimine | 8/1 | water | 50 | 30 | 95.1 |
| 9 | ethyleneimine | 8/1 | water | 50 | 60 | 95.0 |
| 10 | hydroxyethyl ethyleneimine | 5/2 | water | 70 | 50 | 94.6 |
| 11 | AEEI/EI | 4/1 | water | 50 | 50 | 97.3 |
| 12 | ethyleneimine | 4/3 | water | 52 | 50 | 92.7 |
| 13 | ethyleneimine | 1/1.64 | water | 58 | 50 | 60.5 |

Az: aziridine compound, MA: methacrylic acid, IPA: isopropyl alcohol, water.IPA: mixture of water and IPA (50/50 by weight), and AEEI/EI: aminoethyl ethyleneimine/ethyleneimine (90/10 by weight).

COMPARATIVE EXAMPLE 1

The preparation of 2-AEMA was examined by the use of a reaction solvent containing no water.

First, 86 grams of MA, 108 grams of isopropyl alcohol as reaction solvent and 172 milligrams of methoquinone as polymerization inhibitor were placed into a reaction vessel and mixed, and then heated to 50° C. 21.5 grams of EI was introduced into the mixture dropwise in about 1 hour while keeping the temperature at 50° C. Next, the reaction mixture was maintained at a temperature of 50° C. for 3 hours for aging, whereby 2-AEMA were obtained. The reaction solution was analyzed by liquid chromatography, and the selectivity of EI was 30.4 percent. The reaction conditions and results are presented in Table 2.

portion of water to a total weight of the reaction mixture is in the range from 5 to 90 weight percent.

3. The process as defined in claim 1, wherein the ratio of $F_M/F_A$ is in the range from ½ to 20/1, $F_M$ representing the total number of moles of the methacrylic acid introduced, and $F_A$ representing the total number of moles of the aziridine compound introduced.

4. The process as defined in claim 1, wherein the reaction is carried out while maintaining the ratio of $C_M/C_A$ at least at 1.5, wherein $C_M$ represents a molar concentration of the methacrylic acid and $C_A$ represents a molar concentration of the aziridine compound.

5. The process as defined in claim 4, further comprising the steps of:

adding an inorganic acid to the reaction mixture; and carrying out the reaction while keeping a ratio of A/B at least at 1.5,
wherein A is an equivalent of free methacrylic acid and B is an equivalent of base of the aziridine compound in the reaction mixture.

6. The process as defined in claim 1, wherein said aziridine compound is selected from at least one member of the group consisting of ethyleneimine, propyleneimine, hydroxyethyl ethyleneimine, cyanoethyl ethyleneimine, and aminoethyl ethyleneimine.

7. A process for preparing 2-aminoethyl esters of methacrylic acid comprising reacting methacrylic acid and an aziridine compound in a reaction solvent medium selected from the group consisting of water and an aqueous solvent at a temperature in the range of from 10° C. to 100° C., wherein a proportion of water to a total weight of the reaction mixture is in the range from 5 to 90 weight percent, and wherein the ratio of $F_M/F_A$ is in the range from ½ to 20/1, $F_M$ representing the total number of moles of the methacrylic acid introduced, and $F_A$ representing the total number of moles of the aziridine compound introduced.

8. A process for preparing 2-aminoethyl esters of methacrylic acid comprising reacting methacrylic acid and an aziridine compound represented by the formula:

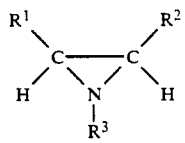

wherein $R^1$ and $R^2$ are respectively selected from the groups consisting of H and an alkyl with 1-4 carbon atoms, and $R^3$ is selected from the group consisting of H, an alkyl with 1-6 carbon atoms, an aralkyl with 7-12 carbon atoms, a cyanoalkyl with 2-6 carbon atoms, a hydroxyalkyl with 1-6 carbon atoms, and an aminoalkyl with 1-6 carbon atoms, in a reaction solvent medium selected from the group consisting of water and an aqueous solvent, at a temperature in the range of from 10° to 100° C.

9. A process for preparing 2-aminoethyl esters of methacrylic acid comprising reacting methacrylic acid and an aziridine compound selected from at least one member of the group consisting of ethyleneimine, propyleneimine, hydroxyethyl ethyleneimine, cyanoethyl ethyleneimine, and aminoethyl ethyleneimine in a reaction solvent medium selected from the group consisting of water and an aqueous solvent at a temperature in the range of from 10° to 100° C.

* * * * *